United States Patent [19]
Frame et al.

[11] Patent Number: 5,281,293
[45] Date of Patent: Jan. 25, 1994

[54] DEVICE FOR LIFTING AND PROCESSING LATENT FINGERPRINTS OR OTHER EVIDENCE

[76] Inventors: Curtis C. Frame, 2541 S. Washington, Pearland, Tex. 77581; Arthur B. Moore, 2400 Loop 35 Apt. 1503, Alvin, Tex. 77511

[21] Appl. No.: 895,119
[22] Filed: Jun. 8, 1992
[51] Int. Cl.⁵ .............................. B32B 31/00
[52] U.S. Cl. ........................ 156/276; 156/60; 156/579; 118/31.5; 427/1
[58] Field of Search ............... 118/31.5; 51/392; 156/60, 64, 276, 579; 283/78; 356/71; 427/1

[56] References Cited
U.S. PATENT DOCUMENTS

| | | | |
|---|---|---|---|
| 1,937,575 | 12/1933 | Joyce | 118/31.5 |
| 1,951,203 | 3/1934 | Pitman | 118/31.5 |
| 2,031,292 | 2/1936 | Walters | 51/392 X |
| 2,459,893 | 1/1949 | Peterson | 51/392 X |
| 2,986,831 | 6/1961 | Terek et al. | 427/1 X |
| 3,192,678 | 7/1965 | Buratti | 51/392 X |
| 3,897,749 | 8/1975 | May et al. | 118/31.5 |
| 4,176,205 | 11/1979 | Molina | 427/1 |
| 4,297,383 | 10/1981 | Bourdon | 427/1 |
| 4,304,398 | 12/1981 | Crowell | 269/48.1 |
| 4,379,178 | 4/1983 | Meadows | 427/1 |
| 4,381,159 | 4/1983 | Payne | 401/118 |
| 4,556,579 | 12/1985 | Lowell | 427/1 |

OTHER PUBLICATIONS

Criminal Justice Monograph vol. V, No. 2 by Robert D. Foote pp. 11-12.
Personal Identification by Harrison C. Allison pp. 284-289.

*Primary Examiner*—David A. Simmons
*Assistant Examiner*—Mark A. Osele

[57] ABSTRACT

A device for applying lifting tape to imaged residues, such as latent fingerprints, is provided which comprises an arcuate base member with a means for providing a rocking motion to the arcuate base member, and with means for releasably attaching lifting tape to the outside surface of the arcuate member with the lifting surface of the lifting tape facing away from the arcuate member whereby it is applied to an imaged residue by a rocking motion of the device when in contact with the imaged residue.

22 Claims, 3 Drawing Sheets

DEVICE FOR LIFTING AND PROCESSING LATENT FINGERPRINTS OR OTHER EVIDENCE

FIELD OF THE INVENTION

Devices for applying, lifting, and further handling of film or tape used in lifting evidence, such as latent fingerprints, glove prints, or other such residues.

BACKGROUND OF THE INVENTION

It has been normal practice for many years for police officers and other investigators to apply powder, chemicals or other image formers onto various surfaces in search of latent fingerprints, glove prints, footprints, and other evidence or residues. Even though photographs are usually taken of formed images before they are lifted, the images are often "lifted" to preserve the images. The lifted images are often used for forensic study in a crime lab or other site which is remote from the scene where the prints are lifted.

The term "latent" was originally used in describing fingerprints, and the like, which were not clearly visible, but that term is now used on virtually any prints which are left on a substrate other than a print card or other residue made directly from a person or source. A latent print image can be compared with a print card in identifying a person or compared with other images taken directly from a known source.

Latent fingerprints are classified into three categories: those which are visible, e.g., those made by skin covered with other substances such as wet paint, blood, ink, mud; invisible prints left by bare skin in contact with a smooth surface, leaving only a perspiration or natural body oil impression; and plastic prints such as those made on soft substances such as dust, grease, wax, soap, putty, asphalt, and the like. Investigators are familiar with the various types of prints and the manner in which imaged residues of latent prints or other evidence are prepared for lifting by using films or sheets used for that purpose.

Among the various films or sheets used in lifting latent images are tapes having a tacky surface, known as "sticky tapes", or can be metal foil, especially silver foil used in lifting chemical residues, such as those used in lifting iodine fumed prints. Lifting tapes may be transparent, opaque, plastic, paper, and some are sheets, such as sheets of rubber having a sticky surface similar to an innertube patch which has a removable layer covering the sticky surface of the rubber.

Also used are "hinged" lifters which are comprised of three pieces of plastic that are bound on one side by a sheet of paper, one of the plastic sheets having an adhesive substance on one side which is protected by another sheet of plastic, and an outer sheet of plastic which serves as the back of the "book" after lifting. The protective sheet of plastic is removed to reveal the sticky surface for lifting a print, then the protective outer surface is used to cover the lifted print on the sticky surface.

Among the materials used for imaging the latent residues are various powders of very fine particle size, appropriate powders being selected on the basis of type of substrate and darkness of the substrate. Commonly used are very finely grained adhesive compounds, often on an aluminum base. "Dragon's blood", a red powder, is very resilient when heated and is often used.

Fluorescent powders are useful for imaging residues on multicolored surfaces which, when exposed to ultraviolet light in darkness, can be photographed without losing contrast to the multicolored surface.

Means have been developed for lifting images of virtually any latent residue, including gloveprints, shoeprints, and skinprints as well as fingerprints.

As used herein, and for purposes of conciseness, the expression "lifting tape" includes any of the films, foils, tapes, or sheets which are applicable for lifting imaged latent residues from surfaces; "imaged residues" means the same as "imaged latent residues" which are of interest in investigations of the type performed by police officers and other such investigators.

The process of applying a lifting tape normally involves cutting a piece, from a roll or sheet, to a size appropriate for the size of the image to be lifted, carefully smoothing it onto the imaged area while trying to avoid wrinkles or bubbles. Then when the lifting tape is applied to another substrate to preserve it, the operator is again faced with trying to lay it down without having it wrinkle or form bubbles. One difficulty often encountered is that of accurately lifting an imaged residue from a curved surface such as a glass, telephone, club, post, doorknob, pipe, and the like.

It is an object of the present invention to provide a device for applying a lifting tape to an imaged residue in a manner which substantially removes the chances of forming wrinkles or bubbles, especially from curved surfaces, including, e.g., but not limited to, the inside surface of a hollow item such as a bucket, bowl, glass, cup, and the like.

It is further object of the present invention to provide a device which, after lifting of an imaged residue with a lifting tape, can be used to smoothly deposit the lifting tape onto another substrate without encountering wrinkles or bubbles in the lifting tape during the depositing step.

SUMMARY OF THE INVENTION

The present device for applying lifting tape in the lifting of an imaged residue comprises a substantially rigid member with a smoothly arcuate surface having means for holding a lifting tape against the outer periphery of the arcuate surface with the image-lifting surface of the tape facing away from the arcuate surface, and with means for grasping the device while using a rocking motion in applying the lifting tape to an imaged residue. A preferred embodiment comprises a resilient pad between the arcuate member and the lifting tape.

In applying the device of the present invention it is found that the lifting tape is easily applied to appropriate imaged residues and substantially avoids getting wrinkles or bubbles in the lifted image. Afterward the lifting tape, carrying the lifted image, is then easily mounted onto another substrate or holding device or otherwise disposed without having wrinkles or bubbles in' the tape.

BRIEF DESCRIPTION OF DRAWINGS

In describing the attached drawings, the word "bottom" is used in describing the orientation of such a device when positioned for lifting prints from a horizontal surface, such as the top of a table. It is of course possible to operate the device in other positions, such as "upside down" when lifting prints from an underside surface or oriented sideways for lifting prints from a vertical surface. The lifting tape may be also referred to at times as a film. Also, figures shown in "elevation" are side views vis-a-vis viewing of the edges of the arcuate member and the tape positioned on the arcuate member

FIG. 1 depicts a side view of an arcuate member (1) holding a lifting tape (2) and a handle (3). FIG. 1a is a top view of FIG. 1.

FIG. 2 depicts a side view of an arcuate member (1) holding a lifting tape (2) and a different type of handle (3) than in FIG. 1. FIG. 2a is a top view of FIG. 2, FIG. 3 depicts a side view which is similar to FIG. 1 and FIG. 1a except that besides arcuate member (1), lifting tape (2) and handle (3), there is also depicted a resilient layer (1a) which is co-extensive with the arcuate member (1) and is positioned between arcuate member (1) and lifting tape (2), with a holding frame member (8) to hold a roll (9) of lifting tape (2), and clamp means (4) having spring means (7) for holding the end of the lifting tape (2) on the other end of arcuate member (1) and (4).

FIG. 4 depicts a side view of a tape holder/dispenser having an arcuate member (1), with its outer (i.e. "lower") arcuate surface covered by a resilient pad (1a), a handle means 3, and a holder for a roll of tape.

DETAILED DESCRIPTIONS INCLUDING BEST MODE CONTEMPLATED BY THE INVENTORS

The present device for holding the lifting tape can be of many different sizes, depending on the various circumstances one encounters in lifting images residues. They can be quite large for lifting imaged residues from large surfaces, such as desk tops, table tops, walls, and the like, or can be made quite small for use inside tight places, such as inside of glasses or cups. The degree of curvature of the arcuate surface of the device is not especially critical except that it must be great enough that the lifting tape is applied to the imaged residue by "rocking" the device from one end to the other, but not so great as to lack the length desired for the lifting of the imaged residue. After rocking the tape onto the imaged print, the device is lifted from the surface on which the imaged residue had been formed. After that the lifting tape, bearing at least a portion of the imaged residue, can be mounted by a rocking motion onto another substrate for safe-keeping as evidence or for further forensic study or other disposition as the case may be in that particular instance. It will be understood that if one is using a device of the present invention for lifting an imaged residue inside the wall of a cylindrical substrate, then the arc surface of the lifting device would need to be of a size which permits the rocking of the device to be appropriately applied inside the cylinder.

In applying the device of the present invention it is found that the lifting tape is easily applied to appropriate imaged residues without encountering wrinkles or bubbles, and the lifting tape, carrying the lifted image, is then easily mounted onto another substrate or holding device without having wrinkles or bubbles in the tape.

Figure 1A:
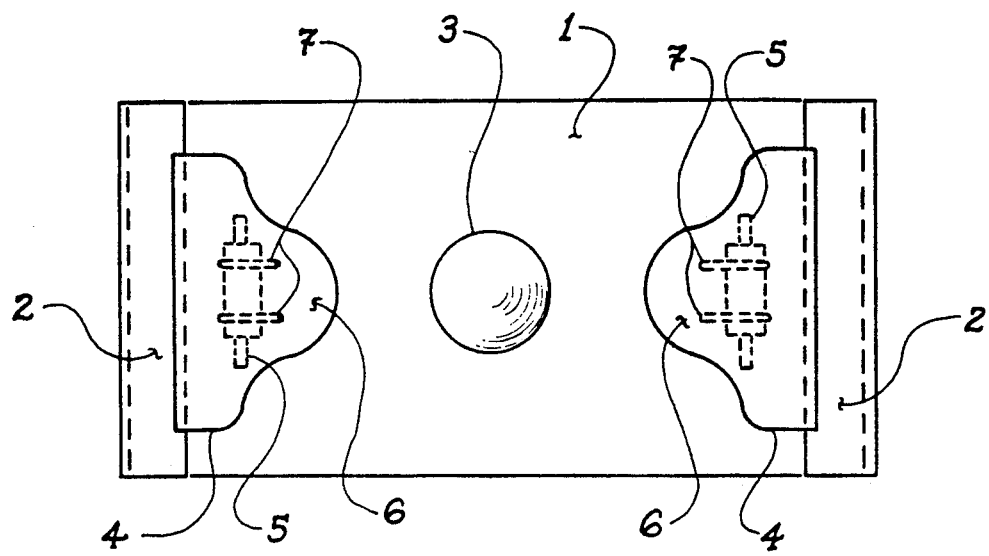
FIGS. 1, 1a, 2, 2a, 3, 4 and 4a are provided for purposes of relating some embodiments of the invention. The figures are not drawn to any particular scale and are intended to be visual aids in relating the invention, not for limiting the invention.
Figure 1:
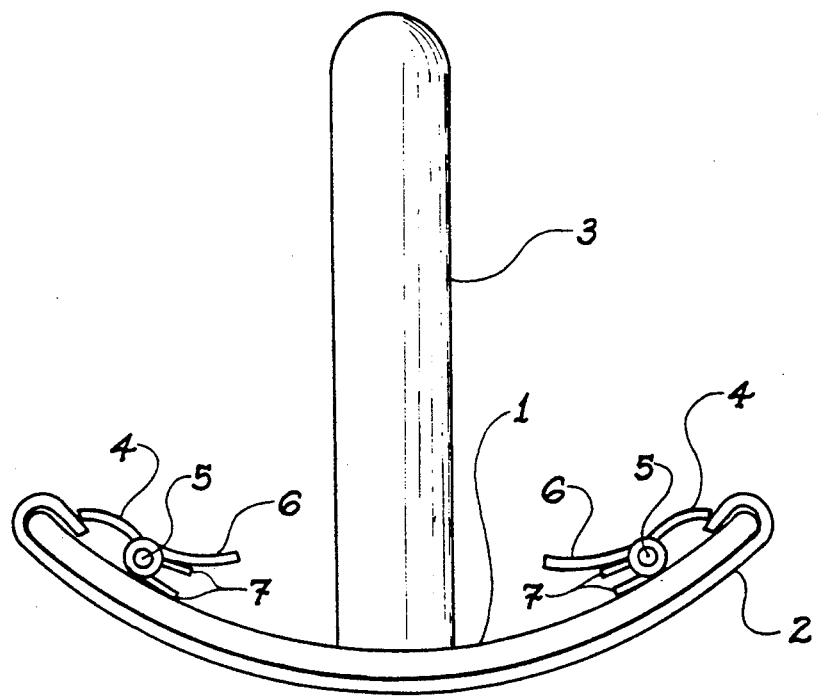

Referring in greater detail to FIG. 1 and FIG. 1a, which are presented here as visual aids in relating elevation and top views, respectively, of certain embodiments of the invention, there is demonstrated a substantially rigid arcuate member (1), having removably affixed along its outer periphery a lifting tape (2), and a handle (3) which can be helpful in grasping the device while rocking the lifting tape from one end to the other to lift an imaged residue. The tape is shown as a finite segment, not on a roll of tape, which is held on each end of arcuate member (1) by clamps (4), each having attachment (5) affixed to the arcuate member (1) as a fulcrum and a lever (6). The tape is held under the clamps (4) by a spring action (7); thus when lever (6) is compressed, such as by thumb pressure, the clamp (4) releases its hold on tape 2).

Figure 2A:
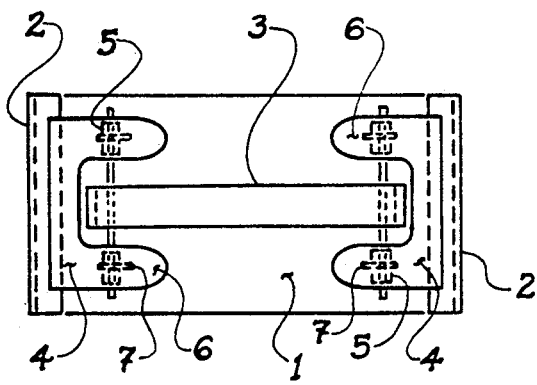
Figure 2:
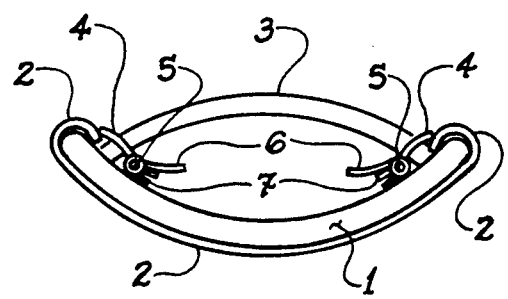

FIG. 2 and FIG. 2a, similar to FIG. 1 and 1a in most respects, also demonstrate an elevation (frontal) and top view, respectively, of a substantially rigid arcuate member (1), having removably affixed thereto a lifting tape (2), and a handle (3) which is useful in rocking the lifting tape from one end to the other to lift an imaged residue from a substrate. In these Figures, the lifting tape (2) is shown clamped to the arcuate member (1) by clamp means (4). The tape (2) can be released from the clamp means (4) by pressing the lever (6) to compress the spring (7).

Figure 3:
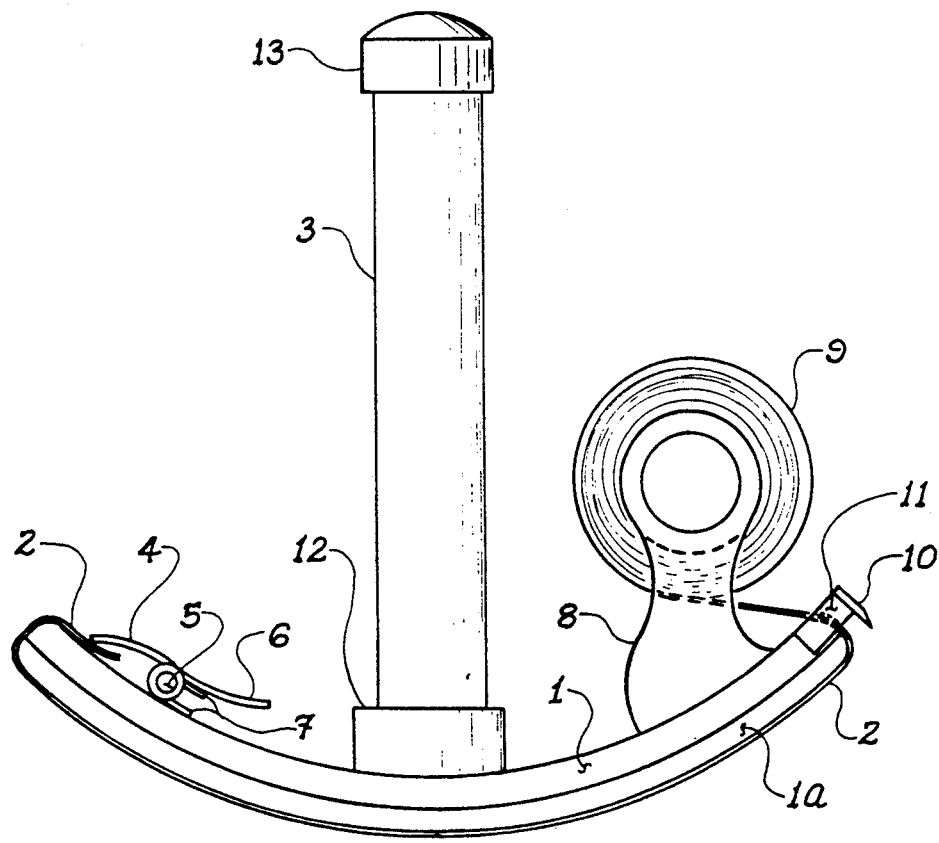

FIG. 3 is a drawing to demonstrate a more complex embodiment of the invention. It is quite similar to FIG. 1 in its basic features of the arcuate member (1), the tape (2) and the handle means (3). It further shows the use of a resilient pad layer (1a) between the lifting tape (2) and the arcuate member (1), and also demonstrates the use of a frame (8) mounted on the arcuate member (1) for holding a roll of lifting tape (9), a clamping means (4) to hold a free end of the tape (2) in place, a clamping means (4) having a spring means (7) affixed at a fulcrum (5) on the arcuate member (1); the clamp holds the tape until it is time to lift the clamp and release the tape by pressing the lever (6) which relieves the spring pressure on the clamp. The holding means (8) comprises cooperating arms, one at each end of tape roll (9), which is made of substantially rigid material, such as plastic, but which flexes enough to permit it to be slightly spreadable enough to allow inserting and removing the tape roll (9). A cutting edge (10), is shown (in edge-view) affixed offset from the end of the arcuate member (1) by the extensions (11) on each side of the the end of the arcuate member. The extensions are thin, but strong, strips which are sturdy enough to hold the blade (10) in position for cutting the lifting tape (2) Alternately, the blade and the fastening strips can be made of a unitary strip of metal which is bent on each end for fastening the blade in an offset position from the end of the arcuate member. The cutting edge (10), provides easy cutting of the tape near the roll of tape for cutting the tape. Also shown in FIG. 3 is an attachment means (12) affixed about mid-point to the inside periphery of the arcuate member for holding handle means 3 in place. The attachment means (12) can be used as a threaded member to receive a threaded handle, or can hold the handle by friction, or the handle can be glued or otherwise permanently affixed to the attachment means (12). Furthermore, the handle can be a knob or other configuration, such as shown in FIG. 2 and, alternatively, the handle can extend outwardly and sideways from the arcuate member instead of sticking straight up as depicted in FIG. 3; such an outwardly extending handle is very convenient in operating the device when lifting an imaged residue from inside a bucket, glass, cup, or the like where the confined space is too small for admitting an investigator's hand. In FIG. 3, an appropriate length of the lifting tape can be reeled off the roll (9) and threaded through the opening provided by off-setting the blade (10) from the arcuate member (1). The tape is positioned against the lower surface of the pad (1a) with the sticky surface of the tape facing away from the pad. The loose end of the tape (2) is held in place by the clamp (4) as the lifting tape is rocked from one end to the other on an imaged print. When it is time to remove the tape from the device, the end is released from the clamp and cut by operation of the cutting blade. The blade can be a sharp blade, such as a knife-like blade, or a serrated blade, such as used when cutting adhesive tape from a roll of adhesive tape.

Figure 4:
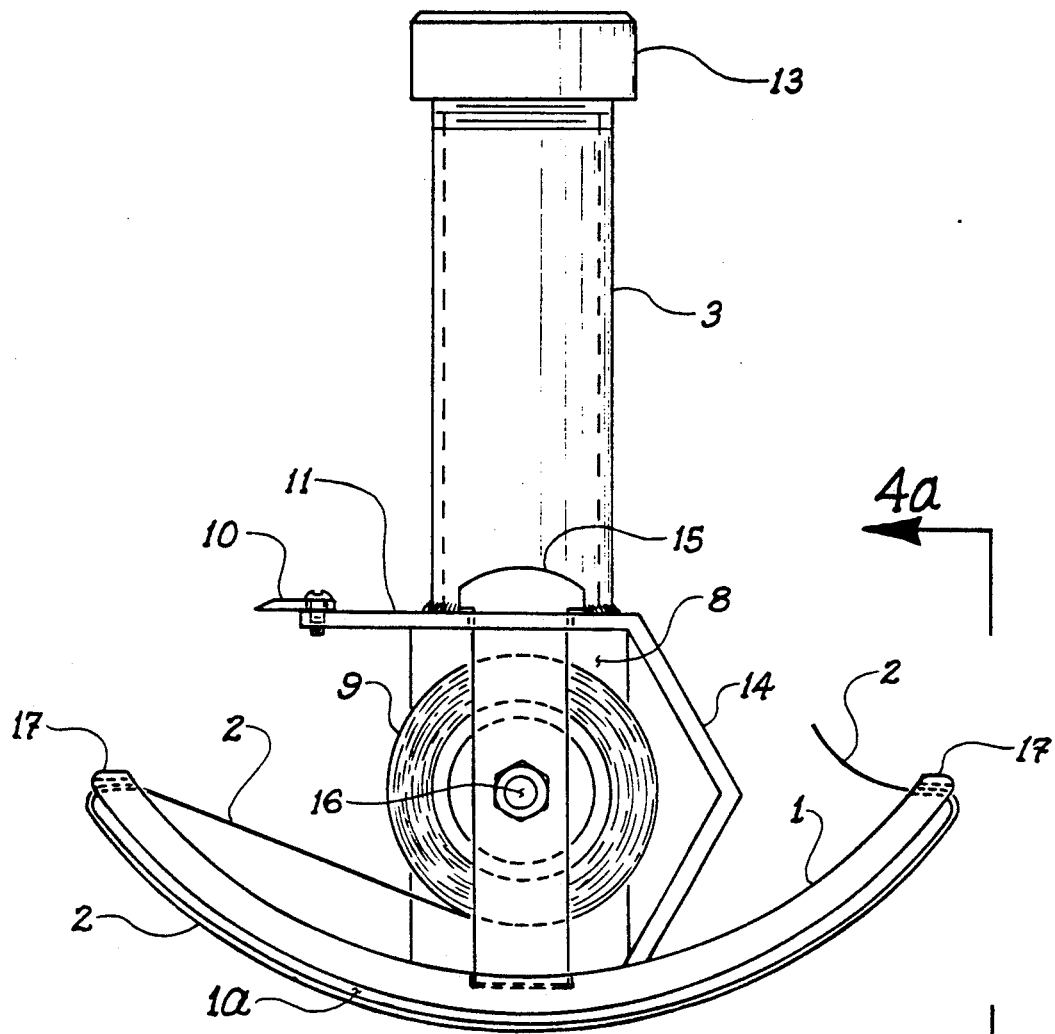
Figure 4A:
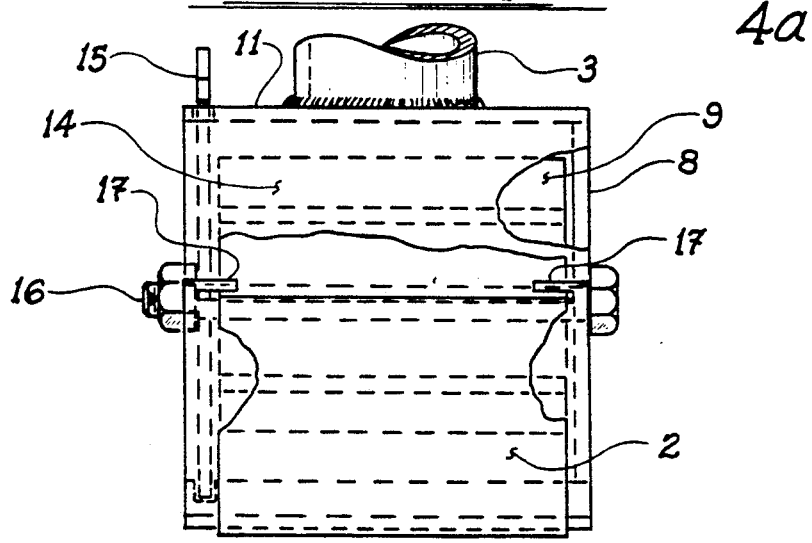

FIG. 4 is a side-view of another more complex embodiment and FIG. 4a is an end-view taken along section 4a—4a of FIG. 4. In FIG. 4 there is the arcuate member (1), the pad member (1a), the lifting tape (2), the handle means (3) shown as being hollow, the tape roll (9), the cutting blade (10), the blade-attachment means (11), a cap (13) for closing the open, top end of the handle (3). Affixed to the arcuate base member (1) there is a fixed frame (8) which, with a superstructure (14), cooperates in supporting the handle (3), the blade attachment means (11), and a spindle means (16) which protrudes through the supporting frame wall (8) on one side and through the support member (15) on the other side for holding a roll of lifting tape. The spindle (16) is partially visible at each end of a cut away portion of FIG. 4a. The spindle is accessed by removing a threaded nut which allows support member (15) to be moved out of the way during loading or unloading of a roll of tape onto the spindle. The hollow handle (3) is a handy place to store dusting powder, dusting brushes, small rubber squeeze bulbs or medicine droppers, or any other small items which one finds useful in preparing imaged prints for lifting. As shown in FIG. 4, a segment of the tape (2) is reeled from the roll (9), passed through guides (17), then across the face of the pad (1a) with its image lifting surface facing away from the pad, and is passed through through guides (17) at the other end of the pad. There the end of the tape can be held in place by hand while performing the rocking motion used for lifting imaged residues, or can be fastened using a clamp as in other figures, or can be held in place by an adhesive from which the tape is easily peeled without harming the lifted imaged residues on the tape.

These figures, not drawn to any given scale, are not exhaustive of the configurations which can be employed in the practice of the present inventive concept. The handle can be made of virtually any material, e.g., wood, plastic, metal, or glass, which has the integrity to withstand the usage expected of it; the same can be said of the arcuate member. The handle can be attached in any suitable manner, including gluing, anchoring, welding (in the case of metals or thermoplastics), bolting or screwing. Any loose end of the tape can be removably affixed to the arcuate member by clamp means of other designs and configurations, or by other means, such as by having a very slightly sticky surface at the interface of the tape and the arcuate member, but which easily releases the tape with a gentle pull without damaging the tape in a manner in which the lifted image is affected.

The resilient pad is most useful when the imaged residue is on a rough or irregular surface, but it is usable when lifting imaged residues from a perfectly smooth surface. The thickness or resiliency of the pad needed can vary over a fairly wide range, but normally would not be expected to be more than about a quarter of an inch. Furthermore, the arcuate member may only be arcuate on its bottom, but can be substantially flat or irregular on top.

EXAMPLE 1

Using a device designed substantially in accordance with FIG. 3, a commonly used, commercially available lifting tape is employed for lifting imaged latent fingerprints from the top of a rusty metal surface which is not entirely smooth. The arcuate outer surface has an arc radius of about 2.5 inches and a width of 3 inches. A 3-inch wide roll of commercially available lifting tape (9) is reeled from the roll, passed through the opening between the arcuate member (1) and the offset cutting blade (10). The tape is positioned along the exposed surface of the pad (1a) with the image lifting surface of the tape facing away from the pad. The tape is fastened at the other end of the arcuate member (1) by using clamp (4) and held there by the spring means (7). The device is used for lifting an imaged latent fingerprint by "rocking" it across the imaged print. Then the device is removed from the surface from which the print was lifted and the sticky surface of the tape is then "rocked" onto another surface to protect and preserve the lifted imaged print and the lifting tape is cut loose from the roll of tape and released from the clip. The image lifting and then the depositing of the tape on another surface is done without encountering wrinkling or bubbling on the lifting tape.

Having the resilient pad between the lifting tape and the arcuate member is a welcome improvement in obtaining useful prints from such a rough surface and the results are better than obtained using the customary manner of applying the lifting tape while smoothing it into place by hand while trying to avoid getting wrinkles or bubbles in the film. Furthermore, when the tape is then transferred onto a card for evidential purposes, the transfer is more easily made without getting wrinkles or bubbles.

EXAMPLE 2

Substantially in accordance with the procedure of Example 1 above, and using essentially the same device and same type of lifting tape, imaged latent fingerprints are lifted from a plastic cover of a book which had numerous surface scratches on it. Here also, better results are obtained than when using the customary method that requires hand smoothing to remove wrinkles and bubbles.

The present invention is not limited to the particular embodiments and examples shown above, and others, having learned of this invention, may incorporate the invention in other embodiments without departing from the purview of the inventive concept of which this invention is comprised. The invention is limited only by the claims which follow.

We claim:

1. In a device for applying a lifting tape to an imaged residue, said device comprising in operable combination, a base which is substantially rigid, said base having an upper portion and an underside portion having an arcuate surface, the said arcuate surface having a width and length sufficient to accommodate a lifting tape provided thereon, means for releasable attachment of a lifting tape, having a lifting surface, to the base so as to conform from end to end along the length of the arcuate surface, with the lifting surface of the lifting tape facing away from the base, and means provided on the upper portion for grasping the device by hand to provide a rocking motion of the base from end to end along the length of the arcuate surface.

2. The device of claim 1 whereon there is provided on the base a means for holding a supply of lifting tape for feeding a selected amount of lifting tape to one end of the arcuate surface, and means at or near the other end of the arcuate surface for fastening an end of a lifting tape.

3. The device of claim 1 whereon a resilient pad is directly affixed to, and conforms to, the arcuate surface and onto which lifting tape can be releasably applied.

4. The device of claim 1 wherein the arcuate portion is made of plastic, wood, metal, glass, refractory, or hard rubber.

5. The device of claim 1 whereon there is affixed on the base a means at or near one end of the arcuate surface for cutting a tape.

6. The device of claim 1 whereon there is affixed on the base a tape clamping means at or near each end of the arcuate surface.

7. The device of claim 1 wherein the imaged residue is a latent skinprint or fingerprint.

8. In a device for applying a lifting tape to an imaged residue, said device comprising in operable combination, a base having a lower portion comprising an arcuate surface which is substantially rigid, and which is smoothly contoured on its outer surface, a smoothly contoured resilient pad affixed to, and conforming to, an effective portion of the outer surface of the substantially rigid portion of the arcuate member, means for attachment of a lifting tape positioned thereon to conform to the outer surface of the resilient pad affixed to the substantially rigid arcuate member whereby the lifting surface of the lifting tape faces away from the arcuate member, and handle means provided on the upper portion of the arcuate member for grasping and providing a rocking motion of the arcuate member.

9. The device of claim 8 whereon there is provided a means for holding a roll of lifting tape by which to feed lifting tape to one end of the outer surface of the arcuate member, and means at the other end of the arcuate member for fastening an end of the lifting tape.

10. The device of claim 8 wherein the arcuate member is made of plastic, wood, metal, glass, refractory, or hard rubber.

11. The device of claim 8 wherein the imaged residue for which the device is used is that of a latent fingerprint.

12. In the process of lifting imaged residues whereby lifting tape is applied to an imaged residue by hand-smoothing the tape into place and then lifting the tape and applying it to another substrate by hand-smoothing, the improvement which comprises the avoidance of such hand-smoothing by use of a device provided for applying the lifting tape in a rocking motion, said device comprising in operable combination, an arcuate member which is substantially rigid, said member having a width sufficient to accommodate lifting tape, said member having an outer arcuate surface and an inner surface, means for attaching lifting tape at or near the ends along the outer arcuate surface of the arcuate member, and handle means for holding the arcuate member with the lifting tape attached thereto and for rocking the device from end-to-end to apply the lifting tape onto the imaged residue and for removing the lifting tape carrying the imaged residue.

13. The process of claim 12 wherein the imaged residue is a skinprint or fingerprint.

14. A method for lifting an imaged residue from a substrate, said method comprising providing an arcuate member having releasably attached along its arcuate surface a lifting tape having a lifting surface facing away from said arcuate member, said arcuate member having a means provided for grasping it and for rocking it from end to end along its arcuate surface, selecting a substrate having on it an imaged residue which is to be lifted, applying the arcuate member in an end to end rocking motion to apply the lifting surface of the lifting tape to the imaged residue to lift the imaged residue, and removing the lifting tape from the arcuate surface.

15. The method of claim 14 wherein there is provided at or near one end of the arcuate member a means for holding a supply of lifting tape for feeding a selected amount of lifting tape along the arcuate surface, and means at or near the other end of the arcuate surface for fastening an end of the selected amount of lifting tape.

16. The method of claim 14 wherein a resilient pad is directly affixed to, and conforms to, the arcuate surface of the arcuate member and onto which lifting tape can be releasably applied.

17. The method of claim 14 wherein the arcuate portion is made of plastic, wood, metal, glass, refractory, or hard rubber.

18. The method of claim 14 wherein the arcuate member is made of plastic or metal.

19. The method of claim 14 wherein there is affixed on the base a means at or near one end of the arcuate surface for cutting a tape.

20. The method of claim 14 wherein there is affixed on the base a tape clamping means at or near each end of the arcuate surface.

21. The method of claim 14 wherein the step of removing the lifting tape from the arcuate surface comprises transferring the lifting tape onto another substrate by using a rocking motion of the arcuate member whereby the lifting surface adheres to such other substrate.

22. The method of claim 14 wherein the imaged residue is a latent skinprint or fingerprint.

* * * * *